United States Patent
Park et al.

(10) Patent No.: US 8,268,552 B2
(45) Date of Patent: Sep. 18, 2012

(54) BIOMOLECULE DETECTOR AND DETECTION METHOD USING THE SAME

(75) Inventors: Tae-sik Park, Suwon-si (KR); Young-il Kim, Suwon-si (KR); Jung-ho Kang, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 877 days.

(21) Appl. No.: 11/323,742

(22) Filed: Dec. 30, 2005

(65) Prior Publication Data
US 2006/0147970 A1    Jul. 6, 2006

(30) Foreign Application Priority Data
Jan. 3, 2005 (KR) .................. 10-2005-0000062

(51) Int. Cl.
C12Q 1/68 (2006.01)
C12M 1/00 (2006.01)
C12M 1/34 (2006.01)
C12M 3/00 (2006.01)

(52) U.S. Cl. ............. 435/6.1; 435/283.1; 435/287.1; 435/287.2

(58) Field of Classification Search ............ 435/6, 6.1, 435/7, 283.1, 287.1, 287.2
See application file for complete search history.

(56) References Cited

U.S. PATENT DOCUMENTS

| | | | |
|---|---|---|---|
| 5,196,350 A * | 3/1993 | Backman et al. | 436/501 |
| 5,316,726 A * | 5/1994 | Babson et al. | 422/65 |
| 6,232,943 B1 * | 5/2001 | Tagawa et al. | 345/97 |
| 2002/0182627 A1 * | 12/2002 | Wang et al. | 435/6 |
| 2003/0068639 A1 * | 4/2003 | Haneder et al. | 435/6 |
| 2003/0132392 A1 * | 7/2003 | Kuroda et al. | 250/397 |
| 2003/0138363 A1 * | 7/2003 | Gao et al. | 422/186 |
| 2004/0037474 A1 * | 2/2004 | Happel | 382/280 |
| 2005/0095599 A1 * | 5/2005 | Pittaro et al. | 435/6 |

OTHER PUBLICATIONS

Jolly, Modern Inorganic Chemistry, 1984, McGraw Hill, p. 52.*
Li et al, Nature Materials, vol. 2, pp. 611-615, available Aug. 24, 2003.*
Austin, Nature Materials, vol. 2, pp. 567-568, Sep. 2003.*
Lo et al, Nanotechnology, vol. 17, pp. 3264-3267 (2006).*
Biance et al, Microelectronic Eng., vol. 83, pp. 1474-1477 (2006).*
The defintion of "screen" provided by the online dictionary at yourdictionary.com.*
Song et al, Science, vol. 274, pp. 1859-1866 (1996).*

\* cited by examiner

Primary Examiner — Robert T. Crow
(74) Attorney, Agent, or Firm — Cantor Colburn LLP

(57) ABSTRACT

Disclosed is a biomolecule detector and a detection method using the same. The biomolecule detector includes a biomolecule chip having a substrate and a slit formed therein. Biomolecules are immobilized on at least a portion of the edges of the slit. A light source directs incident light toward the biomolecule chip, and a screen receives an image formed by a portion of the incident light passing through the slit. The biomolecule detector is small and portable, yet its capability for detecting a target biomolecule is quick, accurate and simple. The simple structural features of the biomolecule detector enable mass production.

27 Claims, 3 Drawing Sheets

BIOMOLECULE DETECTOR AND DETECTION METHOD USING THE SAME

This application claims priority under 35 U.S.C. §119 to Korean Patent Application No. 2005-00062, filed Jan. 3, 2005, hereby incorporated by reference.

BACKGROUND OF THE INVENTION

1. Field of the Invention

The present invention relates in general to a biomolecule detector and a detection method using the same. More specifically, the present invention relates to a biomolecule detector capable of detecting a biomolecule immobilized on a biomolecule chip based on the analysis of diffraction and/or refractivity of light transmitted through the biomolecule chip, and a biomolecule detection method.

2. Description of the Related Art

Recent technical advances in medical science and bioengineering have resulted in growing demands for a biomolecule detector in a broad range of applications including diagnoses of diseases, DNA typing, a forward genetic screen, pathogen detection, new drug discovery and development and so forth.

In general, a biomolecule detector consists of a biomolecule chip and peripherals of the biomolecule chip.

A biomolecule chip is a biological micro chip having biomolecules immobilized on a substrate. Biomolecule chips can be categorized based on the type of immobilized biomolecule, for example DNA chips, protein chips, etc. A biomolecule which is immobilized on a chip and binds with a target biomolecule in a sample is called a probe. Biomolecule chip-related technical fields in development include, for example: biomolecule immobilization techniques for immobilizing biomolecules on a substrate, techniques for binding immobilized biomolecules on a biomolecule chip with components of a sample, and biomolecule detection techniques for detecting the existence and the kind of biomolecules based on the analysis of a biomolecule chip where unknown biomolecules are immobilized.

FIGS. 1 and 2 illustrate a conventional biomolecule detection method and a biomolecule detector. In particular, FIGS. 1 and 2 show a biomolecule detection method and biomolecule detector using Laser-Induced Fluorescence (LIF) as the detection method.

In the LIF detection method, target biomolecules bind to or are labeled with a fluorescent substance. Target biomolecules are then mixed with a probe biomolecule immobilized on a biomolecule chip such that binding can occur between the target and probe biomolecules. Next, unbound (free) target biomolecules are removed, and light from a light source irradiates the biomolecule chip. Lastly, the amount of emitted fluorescence is measured and analyzed to determine the amount of target biomolecules that are bound to the probe biomolecules. A disadvantage of this method is that it requires a preprocessing step for labeling the target biomolecules with the fluorescent substance, which can result in contamination of the target biomolecules. Another disadvantage is that the method requires expensive, large equipment that is not readily portable.

SUMMARY OF THE INVENTION

It is, therefore, an object of the present invention to provide a biomolecule detector for minimizing contamination of a sample, having a small size for portability and a simple structure appropriate for mass production, and a biomolecule detection method using the same.

Disclosed herein is a biomolecule detector, including: a biomolecule chip having a substrate and a slit formed therein. A light source directs incident light toward the biomolecule chip, and a screen receives an image formed by a portion of the incident light passing through the slit.

The slit may be a single slit or a multi-slit.

The substrate may be made of a material that is selected from the group consisting of: non-transparent silicon wafer, glass, and plastic. Also, when using glass for the substrate, the glass is treated with a non-transparent film.

The diameter of the slit is equal to or smaller than about $1 \times 10^{-3}$ m, more preferably, the diameter of the slit ranges from about $1 \times 10^{-20}$ m to about $1 \times 10^{-6}$ m.

The distance between the biomolecule chip and the screen is equal to or smaller than about 0.5 m, more preferably, the distance ranges from about $1 \times 10^{-4}$ m to about $1 \times 10^{-1}$ m.

In an exemplary embodiment, the biomolecules are selected from the group consisting of: antigen, antibody, nucleotide, chelate compound, enzyme, bacteria, yeast, mycobacteria, virus, bacteria pili, bacteria flagella substance, nucleo acid, polysaccharide, lipid, protein, carbohydrate, and hormone.

In an exemplary embodiment, the biomolecule detector further includes: an analysis system connected to the screen.

In an exemplary embodiment, the analysis system comprises: an input unit for receiving data; a database for storing information; an analyzer for analyzing the input data and the information in the database; and a display unit.

In some embodiments, the display unit is selected from the group consisting of: an LCD, a printer, a photosensitive substance, an illumination lamp, and a light for displaying the results.

The light source can be, for example, an LED, a laser beam, a laser diode, natural light, a fluorescent lamp, a filament bulb, an ultraviolet generator, or an infrared generator.

The immobilized biomolecules can be mixed with an externally-provided sample for analysis.

Also disclosed herein is a biomolecule detection method. The method includes directing an incident light beam toward a slit formed in a biomolecule chip substrate, at least a part of the slit having biomolecules immobilized thereon, forming an image on a screen as a result of a portion of the incident light beam passing through the slit, and analyzing the projected image.

In some embodiments, immobilizing the biomolecules the substrate includes immersing the substrate in a solvent containing the biomolecules.

The slit can be a single slit or a multi-slit.

The substrate can be made of a material that is selected from the group consisting of: non-transparent silicon wafer, glass, and plastic. Also, when using glass as the substrate, the glass can be treated with a non-transparent film.

The diameter of the slit is equal to or smaller than about $1 \times 10^{-3}$ m, more preferably, the diameter of the slit ranges from about $1 \times 10^{-20}$ m to about $1 \times 10^{-6}$ m.

The distance between the biomolecule chip and the screen is equal to or smaller than about 0.5 m, more preferably, the distance ranges from about $1 \times 10^{-4}$ m to about $1 \times 10^{-1}$ m.

In some embodiments, the biomolecule is selected from the group consisting of: antigen, antibody, nucleotide, chelate compound, enzyme, bacteria, yeast, mycobacteria, virus, bacteria pili, bacteria flagella substance, nucleo acid, polysaccharide, lipid, protein, carbohydrate, and hormone.

The analysis of the image is carried out by an analysis system connected to the screen.

The display unit can be selected from the group consisting of: an LCD, a printer, a photosensitive substance, an illumination lamp, and a light for displaying the results.

The light source can be selected from the group consisting of: an LED, a laser diode, natural light, a fluorescent lamp, a filament bulb, an ultraviolet generator, and an infrared generator.

In some embodiments, the immobilized biomolecules can bind with an externally-provided sample. In these embodiments, the method further comprises, mixing a sample with the immobilized biomolecules.

The sample can comprise, for example, an antigen, antibody, nucleotide, chelate compound, enzyme, bacteria, yeast, mycobacteria, virus, bacteria pili, bacteria flagella substance, nucleo acid, polysaccharide, lipid, protein, carbohydrate, hormone, or the same biomolecule as those immobilized on the chip.

BRIEF DESCRIPTION OF THE DRAWINGS

The above aspects and features of the present invention will be more apparent by describing certain embodiments of the present invention with reference to the accompanying drawings, in which.

DETAILED DESCRIPTION OF THE PREFERRED EMBODIMENTS

Figure 1:
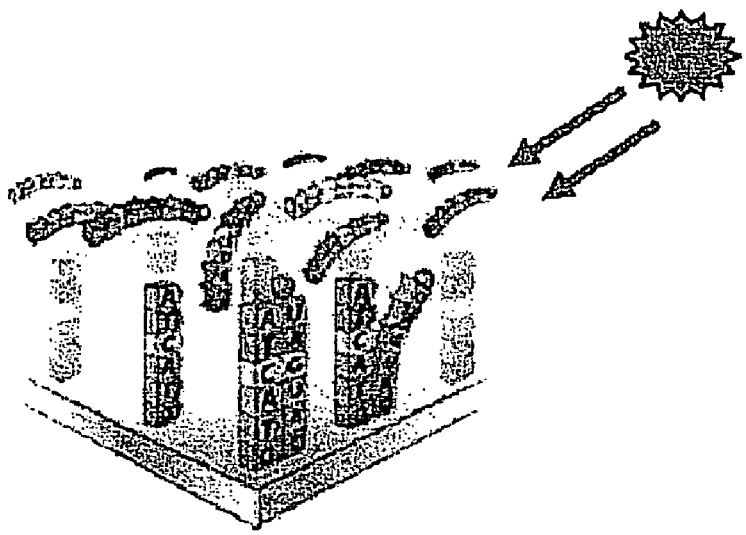
FIG. 1 illustrates a conventional biomolecule detection method based on Laser-Induced Fluorescence (LIF)
Figure 2:
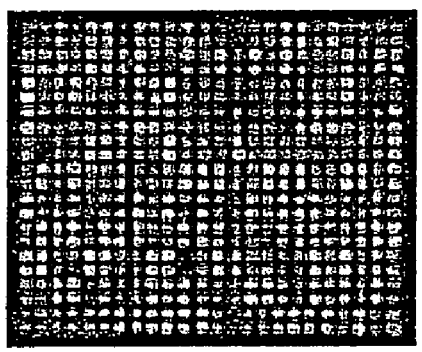
FIG. 2 illustrates a biomolecule detector based on the detection method of FIG. 1.

An exemplary embodiment of the present invention will be described herein below with reference to the accompanying drawings. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

In the following description, the same reference numerals are used to denote the same elements throughout. As used herein, the term "and/or" includes any and all combinations of one or more of the associated listed items. The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 3:
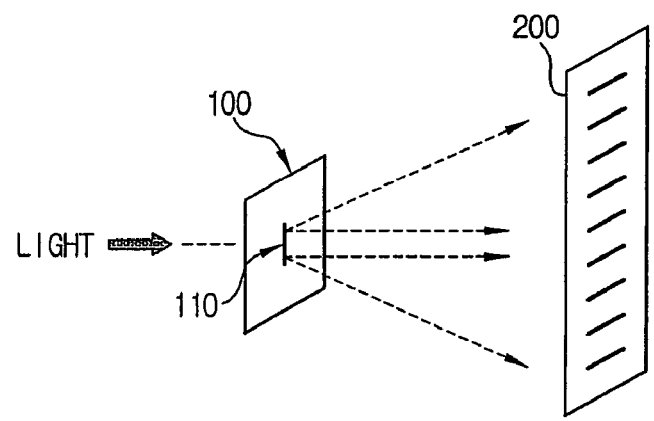
FIG. 3 illustrates a biomolecule detector according to an exemplary embodiment of the present invention.

FIG. 3 illustrates a biomolecule detector according to one embodiment of the present invention.

Referring to FIG. 3, the biomolecule detector includes a biomolecule chip 100 provided with a light source, a slit 110, and a screen 200.

A light beam from the light source is irradiated perpendicularly to the slit 110, and is diffracted as it is transmitted through the slit 110. As a result of this diffraction, destructive and/or constructive interference occurs, and an image is formed on the screen 200.

Figure 4:
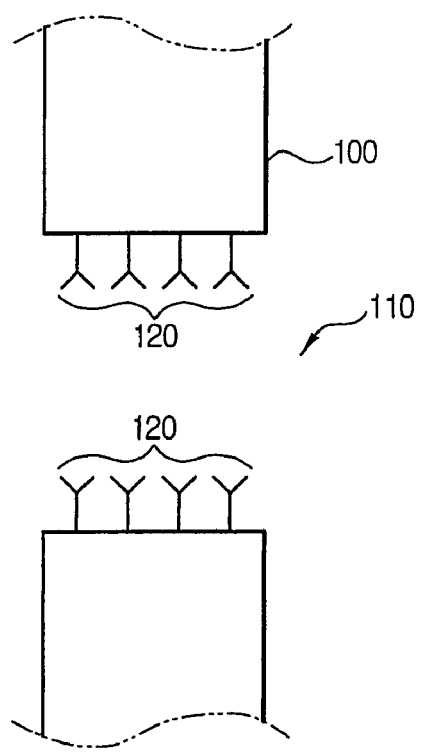
FIG. 4 is an enlarged cross-sectional view of the biomolecule chip shown in FIG. 3.

FIG. 4 illustrates an enlarged cross-sectional view of the biomolecule chip 100.

The biomolecule chip 100 includes biomolecules 120 that are immobilized at the edge of the slit 110. Here, biomolecules 120 are either target biomolecules or probe biomolecules that can bind with the target biomolecules. Either way, the biomolecule detector of the present invention permits detection of the target biomolecules.

In an exemplary embodiment, the biomolecule detection method uses the diffraction characteristics of a light beam transmitted through the slit 110 of the biomolecule detector.

Figure 5:
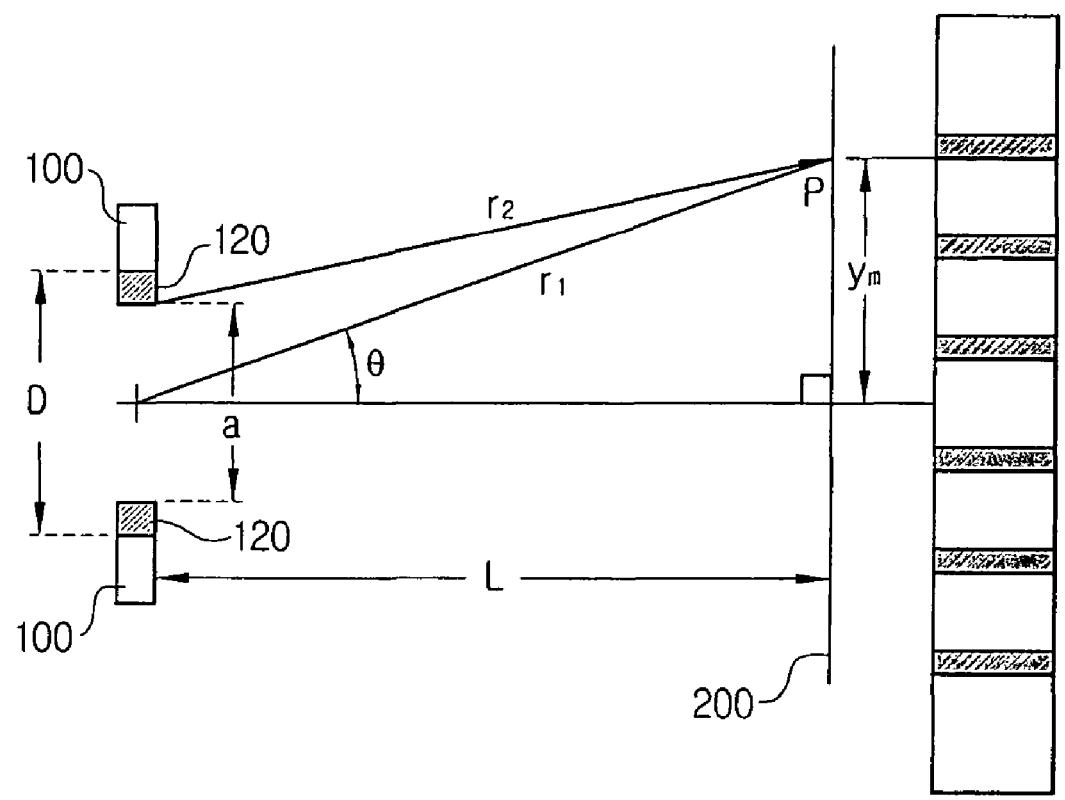
FIG. 5 illustrates a mechanism for biomolecule detection according to another embodiment of the present invention.

FIG. 5 illustrates an exemplary embodiment of a method for biomolecule detection according to the present invention. Referring to FIG. 5, an infinite number of point sources along a straight line of distance d between biomolecules 120 at both edges of the slit 110 propagate spherical waves having the same phase, according to Huygen's Principle.

If the width of the slit 110 is D, the straight line distance between biomolecules 120 at both edges of the slit 110 is a, the angle between the midpoint of the straight line distance between biomolecules 120 and a point P on the screen 200 is θ, the distance between a perpendicular bisector and the point P is $Y_m$, the distance from the midpoint of the straight line distance between biomolecules 120 to the point P is $r_1$, and the distance from the edge of the biomolecule 120 to the point P is $r_2$, then, the path difference of a light beam can be obtained by Equation 1 below.

$$r1 - r2 = \frac{a}{2}\sin\theta \qquad \text{[Equation 1]}$$

Also, the destructive interference condition of a light beam seen at the screen should satisfy Equation 2 below.

$$\frac{a}{2}\sin\theta = q\frac{m\lambda}{2} \qquad \text{[Equation 2]}$$

wherein, θ<1, and sin θ=±mλ/a or $Y_m$=±mλ/a●r1.

Using the above equations, the position of a projected image on the screen can be calculated, and this gives the length of the biomolecule 120 immobilized on the biomolecule chip 100. Based on the length of the biomolecule 120, it becomes possible to detect the kind of the biomolecules 120 on the biomolecule chip 100.

If the biomolecule 120 immobilized on the biomolecule chip 100 is transparent, the biomolecule 120 transmits the light from the light source as it passes through the slit 110, while part of the light passing through the biomolecule 120 is refracted. In this manner, the refractive index, and destructive and/or constructive interference of the diffracted light passing through the slit can be used to detect the biomolecule 120.

As described above, the biomolecule detector of the invention comprises a biomolecule chip, a light source, and a screen.

The biomolecule chip includes a substrate and biomolecules immobilized on the substrate. To be more specific, the biomolecules are immobilized on the edges of a slit formed in the substrate.

The substrate is preferably made of opaque materials so that a light beam emitted by the light source will be transmitted through the slit but not through the surface of the substrate. For example, the substrate of the biomolecule chip can be made of silicon wafer, glass, plastic and the like. Both silicon wafer and plastic are exemplary non-transparent materials.

Similarly, non-transparent glass can be used for the substrate. Where a transparent glass is used, the surfaces of the glass can be treated with a non-transparent film to make the glass opaque.

In the example illustrated, the slit formed on the substrate is a single slit. However, a double slit can be used, although the calculations for determining the length of the biomolecule become more complicated. Thus, the use of a single slit in the substrate permits easier derivation of the detection results.

As mentioned previously, an object of the present invention is to develop a small, easy-to-carry biomolecule detector that is as small and light as possible. For this reason, the biomolecule chip can be fabricated using a microprocessor.

The size (i.e., diameter) of the slit should be about 0.001 m (1 millimeter) or less. In some embodiments, the size of the slit ranges from about $1 \times 10^{-20}$ m to about $1 \times 10^{-6}$ m. With advances in precision technology, however, it is expected that it will be possible to fabricate slits with even smaller diameters.

Any kind of biomolecule to be detected can be immobilized on the biomolecule chip. According to an exemplary biomolecule detection method of the present invention, a target biomolecule present in a sample can be immobilized on a substrate, and detected directly using the biomolecule detector. Alternatively, a probe can be immobilized on the biomolecule chip, mixed with a sample, and bound with a target biomolecule present in the sample to permit detection of the target biomolecule using the biomolecule detector.

The biomolecule to be immobilized on the biomolecule chip can be a target biomolecule or a probe biomolecule. Any known biomolecule can be detected using the present invention. Nonlimiting examples of a suitable biomolecule are an antigen, antibody, nucleotide, chelate compound, enzyme, bacteria, yeast, mycobacteria, virus, bacteria pili, bacteria flagella substance, nucleo acid, polysaccharide, lipid, protein, carbohydrate, and hormone.

Any known immobilization method can be used to immobilize the biomolecules on the substrate. In some embodiments, the immobilization method immerses the substrate in a biomolecule-containing solution, and allows the biomolecules to be immobilized onto a predetermined area of the slit formed in the substrate.

The light source is located perpendicularly to the slit and irradiates light towards the slit, so that the light passes through the slit perpendicularly thereto.

Examples of a suitable light source for use in the biomolecule detector of the invention include an LED, laser diode, natural light, fluorescent lamp, filament bulb, ultraviolet generator, and an infrared generator. Any light source emitting light that permits calculation of a value determined by the diffraction of the light, without degrading the biomolecules, can be used in the detector and method.

In addition, if the medium of the environment in which the biomolecule detector is used is a liquid, for example water, ultrasonic waves can be used in the detection method instead of light waves.

In the present embodiments, the distance between the biomolecule chip and the screen is preferably equal to or smaller than about 0.5 m. To fabricate a small-size, easy-to-carry biomolecule detector, the gap between the chip and the screen should be as small as possible. In some embodiments, a preferable range for the gap is from about $1 \times 10^{-4}$ m to about $1 \times 10^{-1}$ m.

Referring back to FIG. 3, although the light source and the screen 200 are shown located on opposite sides of the biomolecule chip 100, they can be put on the same side if desired.

According to the present invention embodiments, the biomolecule is detected by analyzing the projected image on the screen and calculating Ym. To facilitate these calculations, an analysis system can be connected to the screen for an analysis of the projected image thereon.

The analysis system may include, for example an input unit for receiving data, a database for storing information, an analyzer for analyzing the input data and the information in the database, and a display unit for displaying analysis results.

The analysis system can be provided as a peripheral device for a computer, or as a small-sized terminal. The display unit of the analysis system should be able to show the detection results accurately, quickly, and in an easy to read format for users. Examples of a display unit include an LCD, a printer, a photosensitive substance, an illumination lamp, and light for displaying the results.

The following will now describe an example of the detection method according to the present invention.

EXAMPLE

A silicon wafer substrate was immersed in a sample containing a target biomolecule to fabricate a biomolecule chip. The size of a slit formed in the substrate was $1.03 \times 10^{-6}$ m. The size of the slit after the target biomolecule was immobilized was $1.00 \times 10^{-6}$ m.

Then, a light beam having a wavelength of $5 \times 10^{-7}$ m was irradiated towards the slit of the biomolecule chip.

The distance between the biomolecule chip and the screen was 0.1 m.

After irradiation of the light, the position (Ym) of a projected image on the screen was calculated. The value of $Y_m$ on the screen changed as shown in Table 1 below.

TABLE 1

| Offset position | Before immobilizing biomolecules (m) | After immobilizing biomolecules (m) | Difference |
|---|---|---|---|
| $Y_1$ | 0.0485 | 0.0500 | 0.0015 |
| $Y_2$ | 0.0971 | 0.1000 | 0.0029 |
| $Y_3$ | 0.1456 | 0.1500 | 0.0044 |

The value of the position difference was substituted in the above-described Equation(s) to yield a value for the height of the biomolecule of 30 nm.

After searching several biomolecules having 30 nm in height, the target biomolecule was identified as glucose oxidase.

The biomolecule detector of the present invention is small and portable, yet its capability for detecting a target biomolecule present in a sample is quick, accurate and simple. The simple structure of the biomolecule detector disclosed herein enables mass production and commercialization for a broad range of applications including medical and environmental fields.

The foregoing embodiment and advantages are merely exemplary and are not to be construed as limiting the present invention. The present teaching can be readily applied to other types of apparatuses. Also, the description of the embodiments of the present invention is intended to be illustrative, and not to limit the scope of the claims, and many alternatives, modifications, and variations will be apparent to those skilled in the art.

What is claimed is:

1. A biomolecule detector, comprising:
    a biomolecule chip having a substrate, the substrate including a single slit which comprises at least one inner sidewall and forms an aperture in the substrate;
    biomolecules immobilized on the portions of the at least one inner sidewall forming opposing portions of the single slit;
    a light source configured to direct incident light perpendicularly to the single slit toward the biomolecule chip thus to pass through the single slit;
    a screen onto which an image of the biomolecules directly formed by a diffraction of a portion of the incident light passing through the single slit from the light source is projected and formed; and
    an analysis system connected to the screen, the analysis system being configured to calculate a position of the projected image of the biomolecules on the screen and configured to further calculate a refraction index and a destructive and/or constructive interference by a diffraction of the light passing through the single slit when the immobilized biomolecule are transparent.

2. The biomolecule detector according to claim 1, wherein the substrate is made of a material that is selected from the group consisting of: non-transparent silicon wafer, glass, and plastic.

3. The biomolecule detector according to claim 2, wherein the substrate is a glass treated with a non-transparent film.

4. The biomolecule detector according to claim 1, wherein the length of the single slit is equal to or smaller than $1\times10\text{-}3$ m.

5. The biomolecule detector according to claim 1, wherein the distance between the biomolecule chip and the screen is equal to or smaller than 0.5 m.

6. The biomolecule detector according to claim 5, wherein the distance between the biomolecule chip and the screen is in a range from about $1\times10\text{-}4$ m to about $1\times10\text{-}1$ m.

7. The biomolecule detector according to claim 1, wherein the biomolecules are selected from the group consisting of antigen, antibody, nucleotide, chelate compound, enzyme, bacteria, yeast, mycobacteria, virus, bacteria pili, bacteria flagella substance, nucleic acid, polysaccharide, lipid, protein, carbohydrate, and hormone.

8. The biomolecule detector according to claim 1, wherein the analysis system comprises:
    an input unit for receiving data;
    a database for storing information on the biomolecules;
    an analyzer for analyzing the input data and the information in the database; and
    a display unit.

9. The biomolecule detector according to claim 8, wherein the display unit is selected from the group consisting of an LCD, a printer, a photosensitive substance, an illumination lamp, and a light.

10. The biomolecule detector according to claim 1, wherein the light source is selected from the group consisting of an LED, a laser beam, a laser diode, natural light, a fluorescent lamp, a filament bulb, an ultraviolet generator, and an infrared generator.

11. The biomolecule detector according to claim 1, wherein the immobilized biomolecules are mixed with a sample.

12. A biomolecule detection method, the method comprising:
    directing an incident light beam toward the single slit of the biomolecule detector according to claim 1; forming a projected image on the
    screen as a result of a portion of the incident light beam passing through the single slit; and
    analyzing the projected image.

13. The method according to claim 12, wherein immobilizing the biomolecules comprises immersing the substrate in a solvent containing the biomolecules.

14. The method according to claim 12, wherein the substrate is made of a material selected from the group consisting of: non-transparent silicon wafer, glass, and plastic.

15. The method according to claim 12, wherein the substrate is a glass treated with a non-transparent film.

16. The method according to claim 12, wherein the diameter of the single slit is equal to or smaller than about $1\times10\text{-}3$ m.

17. The method according to claim 16, wherein the diameter of the single slit is in a range from about $1\times10\text{-}20$ m to about $1\times10\text{-}6$ m.

18. The method according to claim 12, wherein the distance between the biomolecule chip and the screen is equal to or smaller than 0.5 m.

19. The method according to claim 18, wherein the distance between the biomolecule chip and the screen is in a range from about $1\times10\text{-}4$ m to about $1\times10\text{-}1$ m.

20. The method according to claim 12, wherein the biomolecules are selected from the group consisting of: antigen, antibody, nucleotide, chelate compound, enzyme, bacteria, yeast, mycobacteria, virus, bacteria pili, bacteria flagella substance, nucleic acid, polysaccharide, lipid, protein, carbohydrate, and hormone.

21. The method according to claim 12, wherein the analysis of the projected image is carried out by the analysis system connected to the screen.

22. The method according to claim 21, further comprising a display unit selected from the group consisting of an LCD, a printer, a photosensitive substance, an illumination lamp, and a light.

23. The method according to claim 12, wherein the light source is selected from the group consisting of an LED, a laser beam, a laser diode, natural light, a fluorescent lamp, a filament bulb, an ultraviolet generator, and an infrared generator.

24. The method according to claim 12, further comprising the step of:
    mixing a sample for analysis with the immobilized biomolecules such that binding between the immobilized biomolecules and target biomolecules present in the sample occurs.

25. The method according to claim 24, wherein the target biomolecule in the sample is selected from the group consisting of antigen, antibody, nucleotide, chelate compound, enzyme, bacteria, yeast, mycobacteria, virus, bacteria pili, bacteria flagella substance, nucleic acid, polysaccharide, lipid, protein, carbohydrate, and hormone.

26. The biomolecule detector according to claim 1, wherein the height of the projected image is indicative of the identity of the biomolecules.

27. The method according to claim 12, wherein the height of the projected image is indicative of the identity of the biomolecules.

* * * * *